United States Patent [19]

Huang

[11] 4,116,996

[45] Sep. 26, 1978

[54] CATALYST FOR METHANE PRODUCTION

[75] Inventor: Yun-Yang Huang, Royal Oak, Mich.

[73] Assignee: Ethyl Corporation, Richmond, Va.

[21] Appl. No.: 803,958

[22] Filed: Jun. 6, 1977

[51] Int. Cl.² .............................................. C07C 1/04
[52] U.S. Cl. ...................... 260/449.6 M; 260/449 M; 252/443; 252/447
[58] Field of Search .................... 260/449 M, 449.6 M

[56] References Cited

U.S. PATENT DOCUMENTS

| 3,842,113 | 10/1974 | Ichikawa et al. | 260/449 M X |
| 3,842,121 | 10/1974 | Ichikawa et al. | 260/449 M X |
| 3,958,957 | 5/1976 | Kuh | 260/449 M X |

*Primary Examiner*—Howard T. Mars
*Attorney, Agent, or Firm*—Donald L. Johnson; Robert A. Linn; Willard G. Montgomery

[57] ABSTRACT

A process for selectively converting a gaseous mixture of carbon monoxide and hydrogen to methane, which comprises contacting the gases with a catalyst at elevated temperature. The catalyst consists essentially of alkali metal, activated carbon and at least one halide of a transition metal selected from Group VIII of the Periodic Table. This catalyst has good activity at temperatures between about 250° C. and about 350° C.

10 Claims, No Drawings

CATALYST FOR METHANE PRODUCTION

BACKGROUND OF THE INVENTION

This invention relates to a catalyst for preparing gases rich in methane by reacting hydrogen with carbon monoxide. Further, the invention relates to a process for preparing such a catalyst, and to a process for reacting hydrogen with carbon monoxide to form methane in the presence of such a catalyst.

The conversion of carbon monoxide or carbon dioxide and hydrogen to methane is known. In a prior art method, a mixture of carbon monoxide or carbon dioxide and hydrogen is contacted with a catalyst comprising a mixture of a carbonaceous solid and an alkali metal compound at a temperature between 427° C. and 816° C.; see U.S. Pat. No. 3,958,957. One particular problem associated with the use of such high temperature catalysts is that the methanation reaction itself is considered to be a combination of several reactions including the primary reaction $$3 H_2 + CO \rightarrow CH_4 + H_2O \quad (1)$$

and secondary reactions (2) and (3)

$$2 H_2 + 2CO \rightarrow CH_4 + CO_2 \quad (2)$$
$$4 H_2 + CO_2 \rightarrow CH_4 + 2H_2O \quad (3)$$

whose thermodynamic equilibria are such that the equilibrium yield of methane is adversely effected at high temperatures, i.e., above 500° C. Accordingly, it would be highly desirable to develop an active catalyst system for methanation at temperatures below 500° C. that would at least in part avoid the difficulties referred to above.

U.S. Pat. No. 3,842,121 discloses contacting a mixture of hydrogen and carbon monoxide at normal temperature and pressure with a catalyst comprising a complex compound of (a) at least one alkali metal belonging to Group IA of the Periodic Table, (b) at least one halide of a transition metal selected from the group consisting of Group IVB, VB, VIB, VII and VIIIB of the Periodic Table and (c) graphite. U.S. Pat. No. 3,842,113 discloses contacting hydrogen and carbon dioxide with a catalyst comprising at least one alkali metal belonging to Group IA of the Periodic Table, graphite and at least one halide of a transition metal selected from the groups consisting of Group VIB and VIII of the Periodic Table under normal temperature and pressure. In both of these processes, however, $C_2$ hydrocarbon, such as ethylene and ethane are the major reaction products.

In accordance with the present invention, it has now been found that high yields of methane can be obtained at temperatures substantially below 500° C. by contacting a gaseous reactant mixture comprising carbon monoxide and hydrogen with a catalyst consisting essentially of an alkali metal, activated carbon and at least one halide of a transition metal selected from Group VIII of the Periodic Table.

SUMMARY OF THE INVENTION

Methane is produced by contacting a gaseous reactant mixture comprising carbon monoxide and hydrogen with a catalyst at an elevated temperature sufficient to convert said mixture to methane; the catalyst consisting essentially of an alkali metal, activated carbon and at least one halide of a transition metal selected from Group VIII of the Periodic Table.

A peferred embodiment of this invention is a process for converting a gaseous reactant mixture comprising carbon monoxide and hydrogen to methane, comprising contacting said gaseous mixture with a catalyst at an elevated temperature sufficient to convert said mixture to methane, said catalyst consisting essentially of (i) an alkali metal, (ii) activated carbon and (iii) at least one halide of a transition metal selected from Group VIII of the Periodic Table.

Another embodiment of this invention is a process for preparing such a catalyst which comprises: (a) preparing an aqueous solution of a halide of a transition metal selected from Group VIII of the Periodic Table, (b) impregnating finely divided particles of activated carbon with the resulting aqueous solution, (c) isolating and drying the resultant mixture, (d) heating the dried mixture to an elevated temperature, preferably between about 100° C. and about 300° C., (e) adding an alkali metal to the activated carbon-metal halide mixture, and (f) heating the resultant mixture at a temperature above the melting point of the alkali metal under reduced pressure to form said alkali metal-activated carbon-transition metal halide catalyst.

The catalyst, according to this invention, comprises (i) at least one alkali metal, (ii) activated carbon, and (iii) at least one halide of a transition metal halide selected from Group VIII of the Periodic Table. The preferred metal halide is the chloride thereof.

The solid particles of activated carbon utilized in the present catalyst are preferably in a finely divided form such as a fine powder. Particles between about 10 and about 100 mesh on the U.S. Sieve Series Scale generally are preferred. The activated carbon utilized in the present invention is further characterized by having a surface area of about 400 m$^2$/gram to about 1400 m$^2$/gram with a surface area of approximately 1300 m$^2$/gram being preferred. This invention contemplates use of halides of any of the Group VIII metals. Particularly useful are the chlorides of iron, cobalt and nickel. Highly preferred is ferric chloride. The utility of the chlorides suggests that bromides or iodides may also be used.

The activated carbon is combined with the Group VIII metal halide to form an intimate mixture of the two by dissolving a water soluble halide salt of a Group VIII metal in an aqueous carrier, impregnating the finely divided particles of activated carbon with the resultant mixture and heating the dried mixture to an elevated temperature between about 100° C. and about 350° C.; preferably between about 100° C. and about 300° C. for a period of time from about 1 to about 20 hours; preferably from about 1 to about 10 hours, and more preferably from about 1 to about 5 hours.

The activated carbon-metal halide mixture is combined with the alkali metal to form an intimate mixture of the two by any means known to physically mix the finely divided particles of the activated carbon-metal halide mixture with the alkali metal. The present invention contemplates the use of any of the alkali metals; however, some are more preferred than others because they are more effective and/or available. Potassium has generally been found to be the most effective. Cubes of alkali metal having dimensions of approximately 1 mm to about 2 mm have been found to be particularly useful in the preparation of the catalyst of the present invention. The dry mixture of activated carbon-metal halide-alkali metal is then heated to a temperature above the melting point of the alkali metal under reduced pressure. The temperature to which the mixture must be heated will, of course, vary depending upon the melting point of the particular alkali metal selected for use in the catalyst. Generally, temperatures between about 150° C. and about 400° C. are preferred, with temperatures between about 250° C. and about 350° C. being more preferred. Preferably, the activated carbon-metal halide-alkali metal mixture is heated for a period of time between about 1 and about 10 hours under reduced pressure, preferably less than $10^{-1}$ mm Hg and more preferably $10^{-3}$ mm Hg. Following heat treatment, helium may be circulated over the resultant mixture to uniformly distribute the alkali metal on the activated carbon-metal halide support. Hydrogen is circulated over the mixture to effect activation thereof. In the catalyst, the weight ratio of transition metal compound to activated carbon is generally about 0.001-1.0:1, preferably 0.01-1.0:1, and the weight ratio of the alkali metal to activated carbon-metal halide compound is generally about 0.05-1.0:1, preferably 0.1-0.5:1.

The reduction of carbon monoxide using the catalyst according to the present invention is generally carried out at a temperature of from about 250° C. to about 350° C., preferably from about 275° C. to about 325° C. under reduced to superatmospheric pressure in a recirculating or passing through system. Although reduction is carried out at temperatures preferably between approximately 250° C. and 350° C., temperatures above and below this range are not to be regarded as being outside the scope of the present invention. Applicant has found, however, that at reaction temperatures below about 250° C., methane formation decreases as temperature decreases. This is shown, for example, in Run 2 of Example I below in which a small amount of methane is formed at a temperature of approximately 205° C. after a period of approximately 1 hour. It is reasonable to believe, however, that a longer reaction time in Run 2 might have resulted in increased methane formation.

Contact between the catalyst and carbon monoxide may also take place utilizing any of the other conventional systems such as a moving bed system, a fluidized bed system or a batch-type operation.

The mole ratio of hydrogen to carbon monoxide in the gaseous reactant mixture is approximately 1:1 to about 10:1, preferably 1:1 to about 3:1 and more preferably about 1.5:1. Approximate conversion of initial carbon monoxide to recovered hydrocarbon is about 3 percent to about 64 percent. The following examples are cited to illustrate the invention, but are not considered as limiting in scope.

EXAMPLE I 1.005 grams of anhydrous ferric chloride was dissolved in 20 ml of distilled water. The solution was added to approximately 9.0 grams of finely divided activated carbon. The mixture was stirred well and dried in the atmosphere for a period of several days. After that, it was dried in an oven at approximately 100° C. for a period of about 3 hours. Approximately 0.645 grams of the activated carbon ferric chloride mixture was then placed in the bottom of a 150 cc glass U-shaped reactor having a side-arm tube. Approximately 0.2 gram of metallic potassium in the form of cubes having dimensions of approximately 1 mm to about 2 mm were placed in the side-arm tube of the reactor and the sample was heated under vacuum from about 25° C. to about 300° C. over a period of approximately 2 hours. The potassium cubes were then melted by a cool flame torch and distilled onto the activated carbon-ferric chloride mixture. Approximately 220 Torr helium was introduced and circulated through the catalyst at approximately 285° C. for about 1 hour to uniformly distribute the metallic potassium on the activated carbon-metal halide support. After brief evacuation, hydrogen was admitted at 500 Torr and circulated through the catalyst for approximately 10 minutes.

A gaseous reactant mixture of hydrogen and carbon monoxide was circulated in the reactor containing the catalyst. The reaction conditions and the results are given in Table I below:

TABLE I

| Catalyst | Activated Carbon/FeCl$_3$/K | |
|---|---|---|
| Run | 1 | 2 |
| Temperature, ° C | 299 | 205 |
| Po, Torr | 590 | 534 |
| H$_2$/CO | 1.39 | 1.51 |
| time, minutes | 13 | 53 |
| Gaseous component | | |
| μ mole | — | 754.4 |
| CO | 640.7 | 8.4 |
| CH$_4$ | 0.8 | 0.3 |
| CO$_2$ | 0.4 | — |
| C$_2$H$_4$ | 3.5 | — |
| CH$_2$H$_6$ | 183 | |
| CH$_4$/C$_2$H$_6$ | | |
| Turnover number | | |
| μ mole CH$_4$/gram min. | 77.0 | 0.25 |

As discussed supra, Run 2 in Table I indicates that methane formation decreases at reaction temperatures substantially below the lower end of the preferred temperature range of the present invention.

I claim:

1. A process for the conversion of a gaseous reactant mixture comprising carbon monoxide and hydrogen to methane, comprising contacting said gaseous mixture with a catalyst at an elevated temperature sufficient to convert said mixture to methane, said catalyst consisting essentially of (i) an alkali metal, (ii) activated carbon, and (iii) at least one halide of a transition metal selected from Group VIII of the Periodic Table, wherein the weight ratio of said transition metal halide to activated carbon is approximately 0.01-1.0:1, and of said alkali metal to activated carbon and transition metal halide is approximately 0.1-0.5:1.

2. A process according to claim 1 wherein said alkali metal is potassium.

3. A process according to claim 1 wherein said transition metal halide is ferric chloride.

4. A process according to claim 1 wherein said hydrogen and said carbon monoxide are contacted at a temperature between about 250° C. to about 350° C.

5. A process according to claim 4 wherein said hydrogen and said carbon monoxide are contacted at a temperature between about 275° C. and about 325°° C.

6. A process according to claim 1 wherein the mole ratio of hydrogen to carbon monoxide is approximately 1.5:1.

7. A process according to claim 1 wherein said catalyst is formed by (a) preparing an aqueous solution of a halide of a transition metal selected from Group VIII of the Periodic Table, (b) impregnating finely divided particles of activated carbon with the resulting aqueous solution, (c) isolating and drying the resultant mixture, (d) heating the dried mixture to an elevated temperature, (e) adding an alkali metal to the activated carbon-metal halide mixture, and (f) heating the resultant mixture at a temperature above the melting point of the alkali metal under reduced pressure to form said alkali metal-activated carbon-metal halide catalyst.

8. A process according to claim 7 wherein said catalyst is formed by (a) preparing an aqueous solution of a halide of a transition metal selected from Group VIII of the Periodic Table, (b) impregnating finely divided particles of activated carbon with the resulting aqueous solution, (c) isolating and drying the resultant mixture (d) heating the dried mixture to an elevated temperature between about 100° C. and about 300° C., (e) adding an alkali metal to the activated carbon-metal halide mixture, and (f) heating the resultant mixture at a temperature to about 350° C. and at a pressure of less than about $10^{-3}$ mm Hg to form said alkali metal-activated carbon-metal halide catalyst.

9. A process according to claim 8 wherein said alkali metal is potassium.

10. A process according to claim 7 wherein said transition metal halide is ferric chloride.

* * * * *

UNITED STATES PATENT AND TRADEMARK OFFICE
CERTIFICATE OF CORRECTION

PATENT NO. : 4,116,996　　　　　　　　　　　　Page 1 of 2
DATED : September 26, 1978
INVENTOR(S) : Yun-Yang Huang It is certified that error appears in the above-identified patent and that said Letters Patent are hereby corrected as shown below:

Column 4, Lines 20-27, Table I:

| Catalyst | | Activated Carbon/FeCl$_3$/K |
|---|---|---|
| Gaseous component $\mu$ mole | | 754.4 |
| CO | | 8.4 |
| CH$_4$ | 640.7 | 0.3 |
| CO$_2$ | 0.8 | -- |
| C$_2$H$_4$ | 0.4 | -- |
| CH$_2$H$_6$ | 3.5 | |
| CH$_4$/C$_2$H$_6$ | 183 | |
| Turnover number $\mu$ mole CH$_4$/gram min. | 77.0 | 0.25 | should read as follows:

UNITED STATES PATENT AND TRADEMARK OFFICE
CERTIFICATE OF CORRECTION

PATENT NO. : 4,116,996                      Page 2 of 2
DATED     : September 26, 1978
INVENTOR(S) : Yun-Yang Huang It is certified that error appears in the above-identified patent and that said Letters Patent are hereby corrected as shown below:

| Catalyst | Activated Carbon/$FeCl_3$/K | |
|---|---|---|
| Gaseous component $\mu$ mole | | |
| CO | -- | 754.4 |
| $CH_4$ | 640.7 | 8.4 |
| $CO_2$ | 0.8 | 0.3 |
| $C_2H_4$ | 0.4 | -- |
| $C_2H_6$ | 3.5 | -- |
| $CH_4/C_2H_6$ | 183 | |
| Turnover number $\mu$ mole $CH_4$/gram min. | 77.0 | 0.25 |

Signed and Sealed this

Sixteenth Day of January 1979

[SEAL]

*Attest:*

RUTH C. MASON
*Attesting Officer*

DONALD W. BANNER
*Commissioner of Patents and Trademarks*